(12) United States Patent
Hoonhout et al.

(10) Patent No.: US 8,892,261 B2
(45) Date of Patent: Nov. 18, 2014

(54) SYSTEM AND METHOD FOR AUTOMATICALLY CREATING A SPECIFIC ATMOSPHERE BY CONTROLLING CONTRIBUTIONS OF SENSORIAL PERCEPTIBLE STIMULUS MEANS

(75) Inventors: Henriette Christine Marie Hoonhout, Eindhoven (NL); Hubertus Maria Rene Cortenraad, Maastricht (NL); Bartel Marinus Van De Sluis, Eindhoven (NL); Elmo Marcus Attila Diederiks, Eindhoven (NL)

(73) Assignee: Koninklijke Philips N.V., Eindhoven (NL)

( * ) Notice: Subject to any disclaimer, the term of this patent is extended or adjusted under 35 U.S.C. 154(b) by 849 days.

(21) Appl. No.: 12/600,505

(22) PCT Filed: May 21, 2008

(86) PCT No.: PCT/IB2008/051986
§ 371 (c)(1),
(2), (4) Date: Nov. 17, 2009

(87) PCT Pub. No.: WO2008/142644
PCT Pub. Date: Nov. 27, 2008

(65) Prior Publication Data
US 2010/0168878 A1  Jul. 1, 2010

(30) Foreign Application Priority Data

May 24, 2007 (EP) .................................... 07108800

(51) Int. Cl.
*G01M 1/38* (2006.01)
(Continued)

(52) U.S. Cl.
CPC ............... *A61L 9/12* (2013.01); *H04L 12/2827* (2013.01); *A61L 2209/12* (2013.01);
(Continued)

(58) Field of Classification Search
USPC .............. 700/275, 8, 90; 84/464 R, 600, 723; 705/10, 14; 706/16, 47; 348/739, 348/815.4; 315/294; 362/101
See application file for complete search history.

(56) References Cited

U.S. PATENT DOCUMENTS 5,949,522 A * 9/1999 Manne ............................ 352/85
6,654,664 B1 * 11/2003 Chiao ........................... 700/239

(Continued)

FOREIGN PATENT DOCUMENTS

| JP | 2004131643 | 5/1992 |
| JP | 2001333410 | 11/2001 |
| WO | 03098971 A1 | 11/2003 |
| WO | 2005105381 A2 | 11/2005 |
| WO | 2006064482 A2 | 6/2006 |
| WO | 2006075299 A1 | 7/2006 |
| WO | WO 2006129250 A1 * | 12/2006 |

*Primary Examiner* — Mohammad Ali
*Assistant Examiner* — Ziaul Karim
(74) *Attorney, Agent, or Firm* — Meenakshy Chakravorty

(57) ABSTRACT

The invention relates to the automatic creation of a specific atmosphere by controlling contributions of sensorial perceptible stimulus means such as lights, sounds, and scents. The invention provides atmosphere settings containing data adapted for controlling the sensorial perceptible stimulus means in order to create at least one specific atmosphere, and atmosphere creation means adapted for automatically controlling the contributions of the sensorial perceptible stimulus means depending on the data contained in the atmosphere settings. Thus, a specific atmosphere may be created automatically without requiring a tedious adjusting of individual contributions of sensorial perceptible stimulus means to the specific atmosphere.

16 Claims, 2 Drawing Sheets

(51) Int. Cl.
*G05B 13/00* (2006.01)
*G05B 15/00* (2006.01)
*G05D 23/00* (2006.01)
*G10H 1/00* (2006.01)
*G10H 3/00* (2006.01)
*H04L 12/28* (2006.01)
*H05B 33/08* (2006.01)
*A61L 9/12* (2006.01)
*H05B 37/02* (2006.01)
*A61M 21/00* (2006.01)

(52) U.S. Cl.
CPC ... *A61M 2021/0027* (2013.01); *H05B 33/0872* (2013.01); *A61M 2205/6054* (2013.01); *A61M 2021/0016* (2013.01); *H04L 2012/285* (2013.01); *A61M 2205/3584* (2013.01); *H04L 12/2816* (2013.01); *A61M 21/00* (2013.01); *A61M 2021/0044* (2013.01); *A61M 2021/005* (2013.01); *H05B 37/0272* (2013.01)

USPC .............................. 700/275; 84/600; 84/723

(56) References Cited

U.S. PATENT DOCUMENTS

| | | | |
|---|---|---|---|
| 7,459,623 B2 * | 12/2008 | Robertson .................. 84/464 R |
| 7,687,744 B2 * | 3/2010 | Walter et al. .................. 219/505 |
| 7,729,941 B2 * | 6/2010 | Zampini et al. .............. 705/14.4 |
| 8,044,769 B2 * | 10/2011 | Diederiks et al. ............ 340/5.64 |
| 2002/0113909 A1 | 8/2002 | Sherwood |
| 2003/0106260 A1 * | 6/2003 | Airaudi et al. ........... 47/58.1 LS |
| 2005/0036300 A1 * | 2/2005 | Dowling et al. .............. 362/101 |
| 2005/0038718 A1 * | 2/2005 | Barnes et al. .................... 705/28 |
| 2005/0185392 A1 | 8/2005 | Walter et al. |
| 2005/0285547 A1 | 12/2005 | Piepgras et al. |
| 2008/0198577 A1 * | 8/2008 | Van Der Poel et al. ....... 362/101 |
| 2008/0249837 A1 * | 10/2008 | Angell et al. .................... 705/10 |
| 2010/0300263 A1 * | 12/2010 | Van De Sluis et al. ..... 84/464 R |
| 2012/0235579 A1 * | 9/2012 | Chemel et al. ................ 315/152 |

* cited by examiner

SYSTEM AND METHOD FOR AUTOMATICALLY CREATING A SPECIFIC ATMOSPHERE BY CONTROLLING CONTRIBUTIONS OF SENSORIAL PERCEPTIBLE STIMULUS MEANS

BACKGROUND OF THE INVENTION

The invention relates to the automatic creation of a specific atmosphere by controlling contributions of sensorial perceptible stimulus means such as lighting means, sound generation means, and scent generation means.

The atmosphere in a given area such as a room or a building is a combination of sensorial perceptible stimuli such as the color and intensity of the ambient light, the ambient temperature, various scents, and the background sound. Technically, it is possible to influence the atmosphere by controlling the contributions of sensorial perceptible stimulus means such as lighting means, sound generation means, and scent generation means, as disclosed in US 2002/0113909 A1. For example, a convenient atmosphere for stimulating the desire to buy something may be created by a suitable background music and a dimmed ambient lighting. Various sensorial perceptible stimulus means for home-use such as multi-color lights for creating an ambient lighting, sound generators for creating a background sound, video displays for creating visual impressions, and scent generators may be controlled by a central processing unit. A user may adjust or program the individual contributions of the stimuli to a desired atmosphere separately, for example by manually adjusting the individual contributions via the central processing unit, which communicates the adjustments to the stimulus means. A beach scene is a typical example for a specific atmosphere with lights adjusted to simulate a sunny day, the sound system producing sounds of waves, and a display such as a television display showing beach scene images. However, the creation of a specific atmosphere by separately controlling contributions of sensorial perceptible stimulus means is tedious and complicated.

Thus, it is an object of the present invention to support a user in creating a specific atmosphere by controlling the contributions of sensorial perceptible stimulus means.

SUMMARY OF THE INVENTION

In order to achieve the object defined above, the invention provides a system for automatically creating a specific atmosphere by controlling contributions of sensorial perceptible stimulus means, wherein the system comprises the following characteristic features:
atmosphere settings containing data adapted for controlling the sensorial perceptible stimulus means in order to create at least one specific atmosphere, and
atmosphere creation means adapted for automatically controlling the contributions of the sensorial perceptible stimulus means depending on the data contained in the atmosphere settings.

In order to achieve the object defined above, the invention further provides a method for automatically creating a specific atmosphere by controlling contributions of sensorial perceptible stimulus means, wherein the method comprises the following characteristic features:
atmosphere settings contain data adapted for controlling the sensorial perceptible stimulus means in order to create at least one specific atmosphere, and
atmosphere creation means automatically control the contributions of the sensorial perceptible stimulus means depending on the data contained in the atmosphere settings.

The characteristic features according to the invention provide the advantage that a specific atmosphere may be created automatically, i.e., without requiring the tedious labor of separately adjusting or programming the sensorial perceptible stimulus means by a user in order to create the desired atmosphere. A user merely has to select the desired specific atmosphere and the corresponding atmosphere settings for creating the desired specific atmosphere. This approach also allows to create a new business model where a user may buy or acquire atmosphere settings, for example over a communication network or as a product add-on. Particularly, atmosphere settings may be used as an incentive to purchase a specific product such as a bottle of Italian wine containing atmosphere settings for creating an Italian like atmosphere in the buyer's home.

It should be noted that the term "atmosphere" used herein relates to the combination of multiple stimuli to the senses of creatures, particularly human beings. Preferably, the atmosphere is created by the combination of different lights, sounds, and scents with different contributions of the stimuli. These stimuli may be easily created by technical means such as multi-color lights, sound generators, and controllable scent generators. Furthermore, the atmosphere may be influenced by altering the temperature as further stimulus.

The term "sensorial perceptible stimulus means" used herein means any technically means for creating specific stimuli which are sensorial perceptible by creatures, preferably human beings. Preferably, sensorial perceptible stimulus means comprise controllable lights, sound generators, and scent generators. "Controllable" means that the stimuli may be automatically controlled by computing or controller means. It also comprises any computing functionality integrated into the stimulus means.

The term "atmosphere settings" used herein means data suitable to be transmitted over communication networks such as the internet and specific for the automatic creation of specific atmospheres. For example, atmosphere settings may be an extensive data set containing the data for controlling the stimuli and also further data such as licenses for a digital rights management system (as will be described later in detail).

The term "specific atmosphere" means a specific combination of certain sensorial perceptible stimulus means and a specific set of contributions of the sensorial perceptible stimulus means, for example a "beach scene" or "French Provence". The beach scene atmosphere may for example combine bright lights for a sunny day, the sounds of waves, and display(s) showing beach scenes. Thus, a specific atmosphere for the beach scene may comprise data about lights, sounds, and displays used as the combination of different stimuli, and data about which lights, which sounds, and which displays are used as the contribution. The French Provence atmosphere may for example combine the mimic of a sunny day with a little bit of purple light created by a light system, a lavender scent created by a scent generator, background sound of crickets produced by a sound system, and a photo of a lavender or sun-flower field on an electronic picture frame. Thus, a specific atmosphere for the French Provence scene may comprise data about lights, scents, sounds, and photos used as the combination of different stimuli, and data about which lights with which intensities, which scents with which intensities, which sounds with which intensities, and which displays are used as the contribution.

The term "atmosphere creation means" comprises any device or apparatus suitable for controlling the sensorial perceptible stimulus means by transmitting control signals to the stimulus means. For example, the atmosphere creation means may be a controller, a personal computer, or a consumer electronics device such as a multimedia center.

According to an embodiment of the invention, mapping means may be provided which are adapted to automatically map input data to specific atmosphere settings and to transmit the specific atmosphere settings to the atmosphere creation means. The input data may be for example a certain code such as a bar code or an internet address such as a uniform resource locator (URL) containing a pointer or link to certain atmosphere settings for download. The mapping of input data to specific atmosphere settings has the advantage that less resources such as storage capacity are required for example on a product carrying the input data. In principle, a bar code may be suitable as input data and mapped to specific atmosphere settings which may be more extensive than the simple bar code. Furthermore, the system of mapping the input data to specific settings allow to store large data sets of atmosphere settings for example on a server in a database while the storage requirements for the input data on the product may be less extensive so that the number of goods suitable as potential data carrier for the input data may be enlarged. Also, the input data mapping has the advantage that products may be used as data carrier which are usually used in environments inappropriate for sensitive data carriers such as electronic or magnetic memories. For example, products containing printed input data may be used in a warm and humid environments such as in a kitchen or a bathroom.

According to an embodiment of the invention, the mapping means may be implemented by a server adapted to receive the input data, to load the specific atmosphere settings corresponding to the input data from a database, and to transmit the specific atmosphere settings to the atmosphere creation means. The server may be a specific server dedicated to the task of mapping, or it may be a standard server computer executing a software for receiving and mapping the input data, loading the corresponding atmosphere settings and transmitting the settings to a specified receiver such as the user's computer or mobile phone.

According to an embodiment of the invention, the server may be an internet server providing the mapping of the input data to the specific atmosphere data as an internet service. This allows to offer the invention to a broad range of consumers. For example, a user may buy a certain product containing a code with input data. The user may enter the code with input data into a web form hosted by an internet site on the internet server providing the service of downloading atmosphere settings associated with the bought product in the internet. Finally, the user may receive the atmosphere settings via an e-mail or a mobile phone message or may download it from the internet server after entering the input data so that the received atmosphere settings may be transmitted to the atmosphere creation means for creating the desired atmosphere. The atmosphere creation means may be directly connected with the computer of the user over which the user has received the atmosphere settings. Thus, the received settings may be automatically transmitted to the atmosphere creation means without requiring further user interaction in order to automatically create the desired atmosphere.

According to a further embodiment of the invention, the atmosphere creation means may be adapted to control the usage of specific atmosphere settings depending on a digital rights management system. For example, the usage of specific atmosphere settings may be coupled to a certain computer of a user, or the usage of the atmosphere settings may be limited according to the digital rights obtained with the atmosphere settings. It is also possible that only registered user may use the atmosphere settings after receiving it. For example, it may be required that user first has to register with an internet service offering atmosphere settings for download. Then, when the user wants to receive a certain atmosphere, she/he accesses the internet service, enters the registration data and, thereafter, the input data printed on the bought product. The internet service personalizes the atmosphere settings so that the user can download and use it only on her/his computer and is not able to forward it to another computer.

According to an embodiment of the invention, the system may further comprise a reader adapted for reading the atmosphere settings or input data from a data carrier containing atmosphere settings or input data, respectively, and to transmit the read atmosphere settings or input data, respectively, to the atmosphere creation means. The data carrier may be a physical storage medium, for example a chip containing the atmosphere settings or input data, respectively, or a printing with the atmosphere settings or input data, respectively. A typical example of a data carrier may be a consumer good such as a bottle of wine or bathing oil. The atmosphere settings or input data, respectively, may then be either stored on a memory chip integrated into the bottle or printed as a code directly onto the bottle or a label of the bottle. In principle, nearly any consumer good or product may serve as data carrier for the atmosphere settings or input data, respectively. Preferably, consumer goods associated with a certain atmosphere such as Italian or French wine may serve as data carrier so that a buyer of such goods can obtain the atmosphere settings as an extra service.

According to a further embodiment of the invention, the data carrier may be a radio frequency identification (RFID) tag. A RFID tag allows a contact less reading of the atmosphere settings or input data, respectively, from a product containing the RFID tag. Thus, a product such as a bottle of wine containing the RFID tag must only be located within the radio frequency detection range of a RFID reader which is then able to automatically read the atmosphere settings or input data, respectively, stored in the RFID tag for creating the specific atmosphere according to the data contained in the atmosphere settings.

Preferably, the sensorial perceptible stimulus means comprise at least one of lighting means, sound creation means, scent generator means. These stimuli are essential for creating atmospheres and may comprise computing equipment in order to be easily controllable by a control computer or controller.

According to a preferred embodiment of the invention, the atmosphere creation means and the sensorial perceptible stimulus means may be connected by a network. The term "network" used herein comprises networks over which control signals and data may be exchanged by several communication partners. For example, a network may be a local area network (LAN), a personal area network (PAN) based on Bluetooth®, or a wireless LAN (WLAN). A network simplifies the connection of the stimulus means with the atmosphere creation means. Furthermore, a network allows to use standard equipment such as a personal computer (PC) as atmosphere creation means and network interface connectors (NICs) integrated into the stimulus means in order to easily connect them with the PC.

According to a further aspect, the invention provides atmosphere creation means adapted for use in a system according to the invention, comprising receiving means adapted for receiving atmosphere settings, processing means programmed to process the data contained in the atmosphere settings and to generate control signals for controlling the sensorial perceptible stimulus means depending on the processed data, and transmitting means adapted for transmitting the control signals to the sensorial perceptible stimulus means connected with the atmosphere creation means.

The atmosphere creation means may be implemented by a computer executing a program implementing the processing means and comprising interface means for a network for transmitting the control signals to the sensorial perceptible stimulus means. The computer may be implemented by a dedicated controller and a memory storing the program. The computer may be also a standard personal computer executing the program implementing the processing means, which is stored in its memory and on its hard disk.

According to an embodiment of the invention, the computer may comprise an internet connection for receiving atmosphere settings downloaded from an internet service providing atmosphere settings.

According to a further embodiment, the computer may comprise a reader interface for connecting with a reader for reading the atmosphere settings or input data from a data carrier containing atmosphere settings or input data, respectively. Preferably, the reader interface comprises a standard interface for connecting computer peripherals such as a universal serial bus interface and a software driver which adapts the interface for communication with the reader for reading the atmosphere settings or input data, respectively.

According to an embodiment of the invention, the method for automatically creating a specific atmosphere by controlling contributions of sensorial perceptible stimulus means may comprise the following steps:

reading input data from a data carrier, transmitting the read input data to a provider of atmosphere settings, mapping the received input data to specific atmosphere settings, transmitting the specific atmosphere settings to the atmosphere creation means, processing the received atmosphere settings in the atmosphere creation means and generating control signals for the sensorial perceptible stimulus means, and transmitting the control signals to the sensorial perceptible stimulus means.

Furthermore, the invention relates to a computer program enabled to carry out the method according to the invention when executed by a computer. The invention also provides a record carrier storing this computer program.

Finally, the invention relates according to an embodiment to a computer programmed to perform a method for creating a specific atmosphere according to the invention and comprising control signal transmission means for controlling one or more sensorial perceptible stimulus means depending on data contained in atmosphere settings.

These and other aspects of the invention will be apparent from and elucidated with reference to the embodiment(s) described hereinafter.

The invention will be described in more detail hereinafter with reference to exemplary embodiments. However, the invention is not limited to these exemplary embodiments.

DETAILED DESCRIPTION

Figure 1:
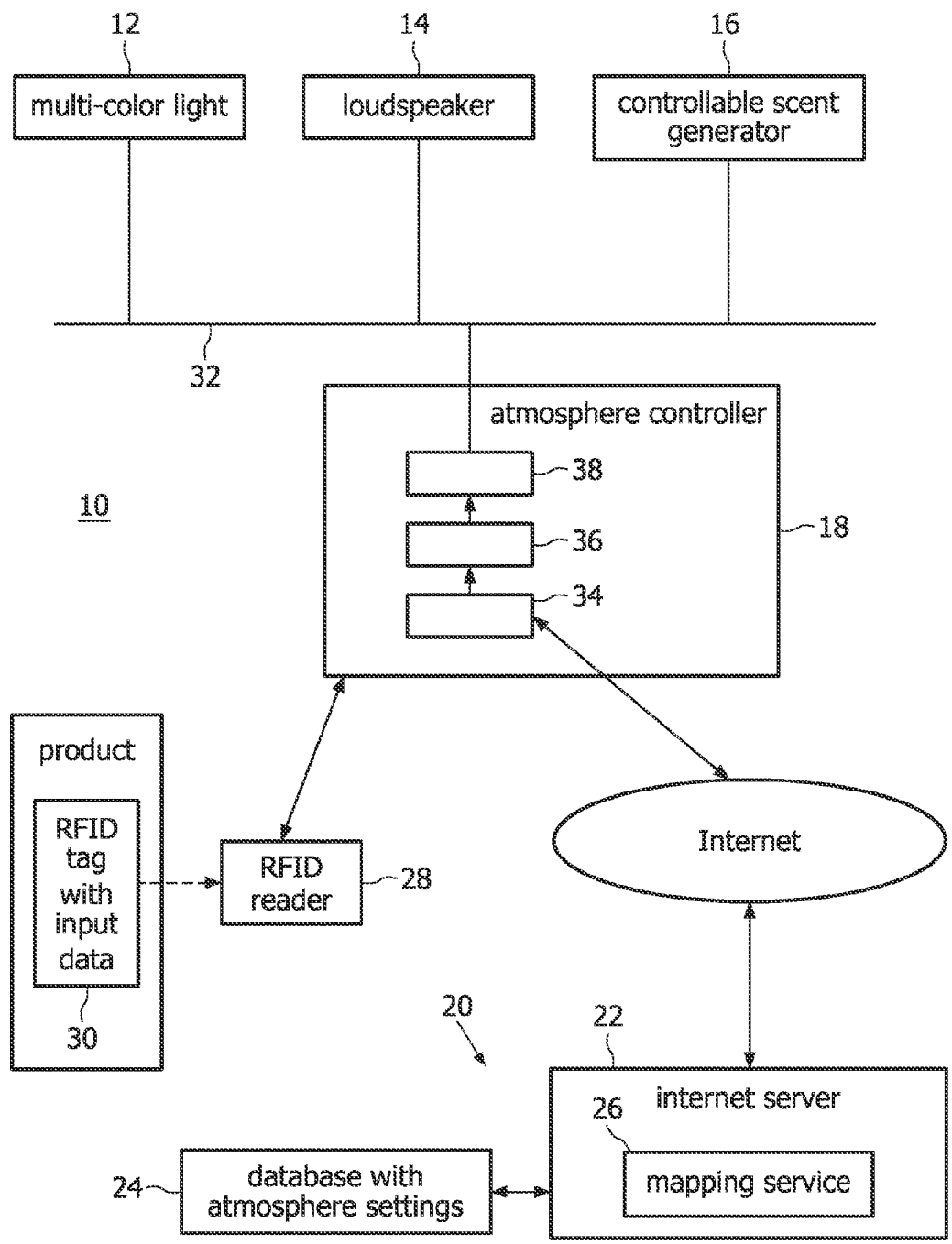
FIG. 1 shows an embodiment of a system for automatically creating a specific atmosphere by controlling contributions of sensorial perceptible stimulus means according to the invention.

The disclosed invention allows to implement a novel business model to deliver specific atmospheres or ambient experience to people when these people buy a product that is generally associated with that specific atmosphere. The business model may be best described by the following example: a person may buy a good bottle of wine from the French Provence. Included with the purchase of the wine may be atmosphere settings of the Provence (technical embodiments follow later). When the person is enjoying the wine at home the atmosphere settings may be activated: a lavender scent is produced, and the lighting system mimics a sunny day, maybe adding a bit of purple light that represents the color of the lavender. The sounds system might produce a background sound of crickets, and for the finishing touch, the electronic picture frame on the wall can show a photo of a lavender or sun-flower field. Such an elaborate atmosphere or ambient experience will be not easy to design by the average person, and therefore selling the professionally designed atmosphere with the wine bottle itself guarantees a matching and optimally designed atmosphere for the associated product.

This business model for delivering atmospheres is of course not limited to bottles of wine. Below is a list of further examples a (not limiting):

A recipe/cook book can have an atmosphere associated with each recipe.

A bottle of liquor. Tequila gives Mexican atmosphere, Vodka gives Russian atmosphere, Ricard gives Mediterranean atmosphere.

Ready-made meals available at the supermarket (only heating up required) can also have an associated atmosphere, for example an Indian atmosphere for an Indian recipe.

Holiday souvenirs gives the atmosphere of the holiday destination where it was bought.

A (children's) book can create the atmosphere in which the story is set.

CD or DVD can have an associated atmosphere that the artist finds appropriate.

Home decorative elements: when you buy bed linen or curtains or paints, you get light scenes with matching/fitting colors.

Relaxing bathing-oils can also come with a complete relaxing scene.

Other: Subscription of seasons settings (spring, summer, Christmas, . . . ) that can be downloaded from a website.

Certain brand of products may give the combined atmospheres with products without any additional costs, and use the atmospheres as a product differentiator. Consumers may also be charged extra for access or usage of the atmosphere settings. Various options are possible:

People need to pay a one time extra for buying the atmosphere settings (e.g. for a specific ready-made meal) and do not have to pay for the next time they use it.

The inventive system charges an atmosphere fee for every time it is being used.

The buyer can use the atmosphere settings a specific amount of times, for instance, a bottle of bathing oil includes atmosphere settings that may be used 20 times.

In addition, there may be content (music, images, video) which is made specifically for the atmosphere-enhancement of the product. On the moment that a user buys the atmosphere settings, he may automatically acquire this content (e.g. a Michael Jackson song when buying the Pepsi atmosphere).

The atmosphere settings information can be physically stored in a storage medium which is packed together with the product or integrated into the product or product package. The atmosphere settings may be also available from the Internet, and the product or product package includes a way to access this information, e.g. by using the product ID or a unique product-specific URL. For instance, a device may be able to determine a unique product ID (e.g. by scanning the bar code or reading the RFID) and use the product ID to retrieve the atmosphere settings from a particular atmosphere provider service on the Internet. The atmosphere-enabled products could carry a clear visual indication or label which communicate to the consumer that atmosphere settings have been defined for the product.

Technically, the atmosphere settings may be distributed as follows (not limiting):

- The Label of a product can contain a link to a web site where the atmosphere settings can be downloaded.
- In a few years many products will contain RFID tags. These tags can contain a link to a web site where the atmosphere settings can be downloaded.
- In the future memory size of the RFID chips will increase. This memory can then contain the atmosphere settings (the complexity of the stored atmosphere scenes depend on the amount of memory available for storing the atmosphere settings on the RFID chip).
- The system in the house of a user may then detect the product by the RFID chip or tag and can download the atmosphere settings from an internet site, automatically or upon request of the user. When appropriate the atmosphere can be set manually by the user or automatically by the system.

According to a further aspect of the invention, the usage of atmosphere settings may be controlled by a digital rights management system, as described in the following:

- The amount of times the atmosphere that comes with the product can be "used" can be regulated. The atmosphere can be used as much as the user wants, or it can be used only a predefined number of times.
- Alternatively, the intensity of the atmosphere can become less intense every time it is used (by controlling the settings). This also implies that the atmosphere can only be used a predetermined amount of times.

The creation of atmosphere settings can be done in various ways:

- Manually for every (combination of) product(s) by atmosphere experts
- Manually for every (combination of) product(s) by a community of atmosphere enthusiasts ("open source atmospheres")
- Automatically, e.g. using a product metadata keywords such as "Italian, diner, spaghetti, exclusive"

In a more advanced scenario, multiple products could be scanned at once, i.e., the atmosphere settings of these products may be read at once, and based on the combination of the atmosphere settings of the different products, appropriate overall atmosphere settings could be generated. For instance, a consumer may want to retrieve the atmosphere by scanning a particular Italian wine, a pasta sauce, and a particular candle. The system should yield atmosphere settings which take the combination of these various atmosphere products into account. In this advanced case, the consumer may be not be charged with a triple atmosphere fee, but only pay a single atmosphere fee, for example.

In the following, the technical implementation of the invention is explained by means of an embodiment of a system and a method for automatically creating a specific atmosphere by controlling contributions of sensorial perceptible stimulus means.

Figure 2:
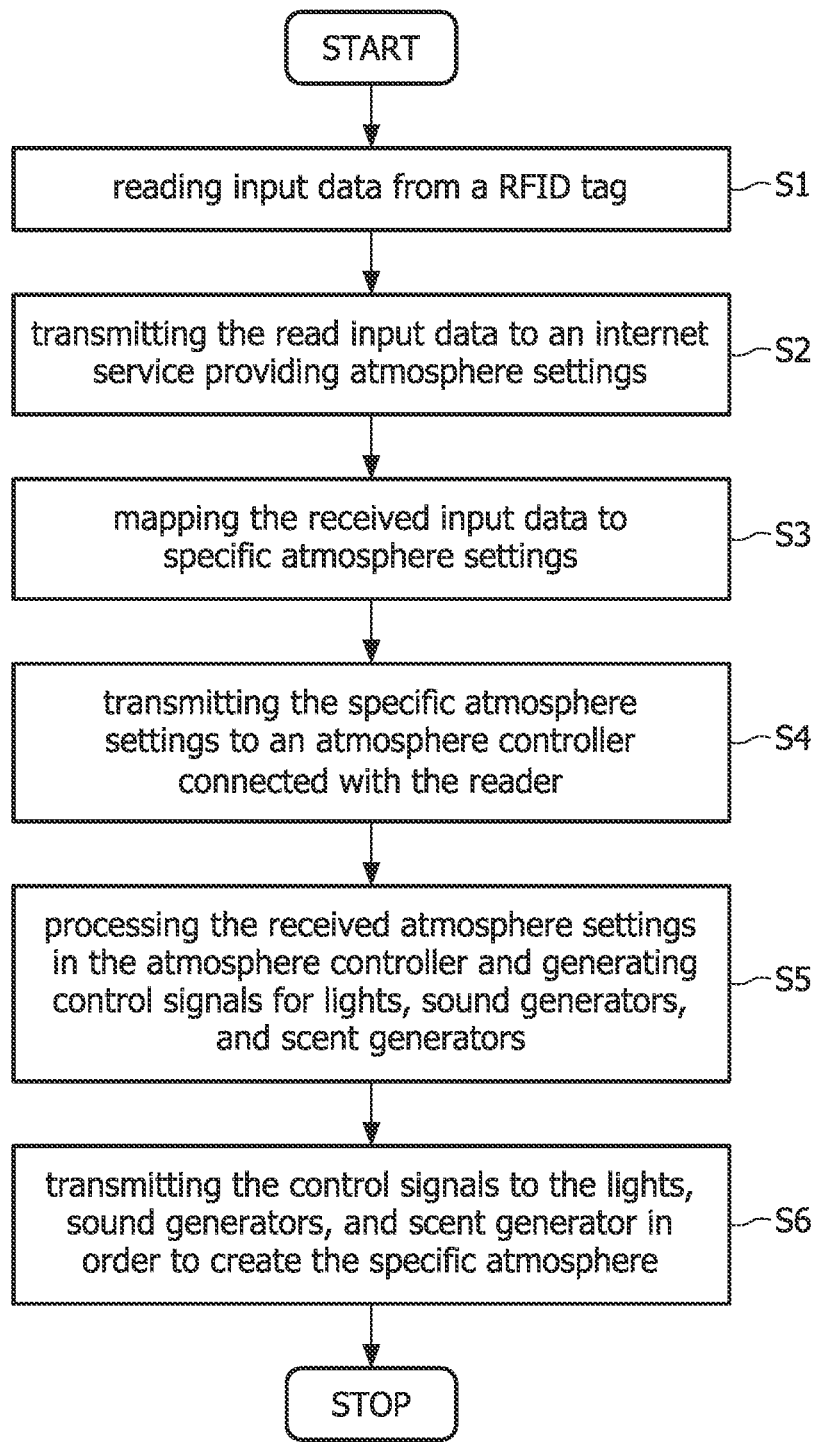
FIG. 2 shows an embodiment of a method for automatically creating a specific atmosphere by controlling contributions of sensorial perceptible stimulus means according to the invention.

The system 10 is shown in FIG. 1. A flowchart of the method is shown in FIG. 2. In the following description, reference is made to both FIGS. 1 and 2.

The system 10 comprises an atmosphere controller 18 serving as atmosphere creation means and a multi-color light 12, a loudspeaker 14, and a controllable scent generator 16 as sensorial perceptible stimulus means. The controller 18 and the means 12, 14, and 16 are connected by a network 32 such as a PAN. The controller 18 is connected with a RFID reader 28.

When a product such as a bottle of wine containing a RFID tag 30 with input data for receiving atmosphere settings is within the radio frequency range of the RFID reader 28, the reader 28 reads the input data from the RFID tag 30 (step S1) and transmits the read data to the controller 18. The controller 18 detects the received input data as data associated with atmosphere settings of the product, and transmits the input data automatically over the internet to an internet service providing atmosphere settings (step S2).

The internet service comprises mapping means 20 for mapping the input data to specific atmosphere settings. The mapping means 20 comprise an internet server 22 providing atmosphere settings as internet service. The internet server 22 calls a mapping service 26 for mapping the received input data to specific atmosphere settings (step S3). The mapping service 26 reads the atmosphere settings associated with the input data from a database 24 with atmosphere settings and returns the read atmosphere settings to the calling internet service. Thereafter, the internet service forwards the read atmosphere settings to the IP address of the controller 18 (step S4).

In the controller 18, receiving means 34 receive the atmosphere settings as TCP/IP data packets, prepares the received data for further processing, for example extracts the essential data from the received TCP/IP data packets, and forward the prepared data to processing means 36 which process the prepared data in that they generate control signals for controlling the means 12, 14, and 16 in order to create the specific atmosphere associated with the input data contained in the RFID tag 30 of the product (step S5). Particularly, the processing means 36 may convert the digital data into control data for directly controlling the stimulus means 12, 14, and 16, such as light intensity control data or audio and video data or scent generator control data. The processing means 36 may also be able to add further data to the atmosphere settings, for example certain sound and video data, particularly when the atmosphere settings merely contain some information or internet links to audio or video data such as a hint to the kind of music to be played as background music or the kind of visual information to be displayed on a video display.

The processing means 36 forward the generated control signals to transmitting means 38 which are able to communicate with the means 12, 14, and 16 over the network 32 and transmit the control signals to the respective means 12, 14, or 16 depending on the type of control signal. For example, the control signals may comprise a signal for controlling the intensities of the different colors of the multi-color light 12, audio signals for the loudspeaker 14, and a scent intensity control signal for the scent generator 16. The transmitting means 38 determines from the received control signals the kind of stimulus means 12, 14, or 16 which is to be addressed, addresses the determined means, for example the loudspeaker 14 in case of audio signals, and transmits the respective control signals to the addressed stimulus means in order to cause them to generate the desired stimulus (step S6).

Thus, the desired atmosphere is created automatically with a minimum of user interaction, though a user may influence the process of creating the desired atmosphere at several different stages, for example when the controller 18 receives the atmosphere settings from the internet, or when the controller 18 transmits the input data over the internet to the internet service for mapping it to a specific atmosphere settings.

The invention has the main advantage that it automatically creates a specific atmosphere and, therefore, does not require tedious adjusting of the individual contributions of sensorial perceptible stimulus means in order to create a specific atmosphere.

The functionality of the invention, particularly the controlling of contributions of the sensorial perceptible stimulus means may be performed by hard- or software. In case of an implementation in software, a single or multiple standard microprocessors or microcontrollers may be used to process a single or multiple algorithms implementing the invention.

It should be noted that the word "comprise" does not exclude other elements or steps, and that the word "a" or "an" does not exclude a plurality. Furthermore, any reference signs in the claims shall not be construed as limiting the scope of the invention.

The invention claimed is:

1. A system comprising an atmosphere controller, the atmosphere controller comprising:
    a reader interface configured to connect with a data input device which is configured to read input data from a data carrier having stored thereon said input data, the input data comprising a reference to a specific atmosphere setting, wherein the data carrier comprises one of a label and an RFID tag attached to one of a product and a product package, wherein the input data stored on the data carrier includes an address of a web site for the Internet service where the specific atmosphere setting can be downloaded to the atmosphere controller;
    an Internet interface configured to send the input data via the Internet to an Internet service and to receive the specific atmosphere setting via the Internet from the Internet service, wherein the input data is mapped to the specific atmosphere setting;
    a plurality of sensorial perceptible stimulus devices, including a multi-color light, a loud speaker, and a controllable scent generator;
    a processor configured to process data contained in the specific atmosphere setting and to generate one or more control signals for controlling the sensorial perceptible stimulus devices depending on the processed data; and
    a transmitter configured to transmit the one or more control signals to the sensorial perceptible stimulus devices.

2. The system of claim 1, further comprising an Internet server configured to implement the Internet service, wherein the specific atmosphere setting is generated by a mapping module residing in the Internet server.

3. The system of claim 2, wherein the mapping module matches the input data with entries in a database of atmosphere settings stored in a memory accessible by the Internet server.

4. The system of claim 1, wherein the transmitter is configured to transmit the control signals to the multi-color light, the loud speaker and the controllable scent generator.

5. The system of claim 4, wherein the one or more control signals comprise:
    a multi-color light control signal;
    a loud speaker control signal; and
    a controllable scent generator control signal.

6. The system of claim 1, further comprising an Internet server configured to implement the Internet service, wherein the specific atmosphere setting is generated by a digital rights management system residing in the Internet server.

7. The system of claim 1, further comprising the data input device.

8. The system of claim 7, wherein the data input device is configured to read the input data from one of a radio frequency identification tag or a bar code.

9. The system of claim 1, wherein the atmosphere controller and the sensorial perceptible stimulus devices are connected by a network.

10. The system of claim 1, where the data carrier is associated with an atmosphere-enabled product and where the input data comprises a product ID or a unique product-specific URL.

11. A method, comprising:
    at an atmospheric controller, reading input data from a data carrier, the input data comprising a reference to a specific atmosphere setting, wherein the data carrier comprises one of a label and an RFID tag attached to one of a product and a product package, and wherein reading the input data from the data carrier includes reading an address of a web site for the Internet service where the specific atmosphere setting can be downloaded to the atmosphere controller;
    transmitting the input data via the Internet to an Internet service configured to provide atmosphere settings;
    receiving the specific atmosphere setting via the Internet from the Internet service, wherein the specific atmosphere setting is mapped from the transmitted input data;
    at the atmospheric controller, processing the received specific atmosphere setting to generate one or more control signals for controlling a plurality of sensorial perceptible stimulus devices, including a multi color light, a loud speaker, and a controllable scent generator, wherein the one or more control signals include a multi-color light control signal, a loud speaker control signal, and a controllable scent generator control signal; and
    transmitting the control signals from the atmospheric controller to the plurality of sensorial perceptible stimulus devices.

12. The method of claim 11, wherein the data carrier is a radio frequency identification (RFID) tag.

13. The method of claim 11, wherein the specific atmosphere setting represents sensorial perceptible stimuli settings comprising a color and intensity of an ambient light control setting, an ambient temperature control setting, a scent control setting, and a background sound control setting.

14. The method of claim 11, where the data carrier is associated with an atmosphere-enabled product and where reading input data comprises reading a product ID or a unique product-specific URL.

15. The method of claim 11, wherein the Internet service is provided by an Internet server, and wherein the specific atmosphere setting is generated by a mapping module residing in the Internet server.

16. The method of claim 15, further comprising the mapping module matching the input data with entries in a database of atmosphere settings stored in a memory accessible by the Internet server.

* * * * *